United States Patent [19]
Wright

[11] Patent Number: 5,670,327
[45] Date of Patent: Sep. 23, 1997

[54] ENZYMATIC METHOD FOR DETECTING A LABELLED SEGMENT AND A SOLUTION OR COMPOSITION THEREFOR

[76] Inventor: Dennis Wright, 3839 Wiggington Rd., Tallahassee, Fla. 32301-3234

[21] Appl. No.: 279,940

[22] Filed: Jul. 25, 1994

Related U.S. Application Data

[63] Continuation-in-part of Ser. No. 10,344, Jan. 28, 1993, Pat. No. 5,354,658.

[51] Int. Cl.$^6$ .................. G01N 33/573; G01N 33/535
[52] U.S. Cl. .................. 435/7.4; 435/6; 435/7.9; 435/7.95; 435/14; 435/207
[58] Field of Search .................. 435/7.9, 14, 19, 435/29, 207, 960, 975, 7.4, 6, 7.95; 436/826, 904

[56] References Cited

U.S. PATENT DOCUMENTS

| | | | |
|---|---|---|---|
| 4,215,197 | 7/1980 | Tarbutton | 435/18 |
| 4,427,771 | 1/1984 | Misaki et al. | 435/22 |
| 4,613,569 | 9/1986 | Geisler et al. | 435/26 |
| 4,642,295 | 2/1987 | Baker | 436/87 |
| 4,645,742 | 2/1987 | Baker | 436/15 |
| 4,748,111 | 5/1988 | Dattagupta et al. | 435/7 |
| 4,847,194 | 7/1989 | Quante | 435/7 |
| 4,847,196 | 7/1989 | Geisler et al. | 435/26 |
| 4,849,347 | 7/1989 | Familletti et al. | 435/26 |
| 4,956,301 | 9/1990 | Ismail et al. | 436/87 |
| 4,978,613 | 12/1990 | Bieniarz et al. | |
| 5,053,336 | 10/1991 | Vanderlaan et al. | 435/240.27 |
| 5,082,780 | 1/1992 | Warren, III et al. | 435/191 |
| 5,139,934 | 8/1992 | Stewart et al. | 435/7.92 |
| 5,188,938 | 2/1993 | Khanna et al. | 435/7.7 |
| 5,354,658 | 10/1994 | Wright . | |

OTHER PUBLICATIONS

Heegaard, Neils H. H., Applied and Theoretical Electrophoresis 1:261-264 (1990) "Visualization of alkaline phophatase by means of formazin staining".

Kugler, P. Histochemistry 75:99–112 (1982) "Quantitative Dehydrogenase Histochemistry . . . ".

Blake et al., Analytical Biochemistry 136:175–179 (1984) "A Rapid, Sensitive Method for Detection of Alkaline Phosphatase-Conjugated . . . ".

Kiyama et al., Neuroscience Research, 9 (1990) 1–21 "Recent progress in the use of the technique of non–radioactive in situ hybridization . . . ".

Boehringer Mannheim Corporation, "Nonradioactive DNA Labeling and Detection Kit" (Nov. 1990).

Bondi, A. et al. Histochemistry, vol. 76, pp. 153–158. 1982.

Celada, F. in Immunoenzymatic Techniques (Feldman, G. et al., eds., Amsterdam: North–Holland Pub. Co.), pp. 83–89. 1976.

Gossrau, R. Histochemistry, vol. 58, pp. 203–218. 1978.

Gossrau, R. et al. in Histochemistry, Theoretical and Applied, 4th Ed. (Pearse, A.G.E., ed., London: Churchill Livingstone), vol. 3, pp. 241–279. 1991.

Terazawa, K. et al. J. Immunoassay, vol. 12, No. 2, pp. 277–292. 1991.

*Primary Examiner*—Mary E. Ceperley
*Attorney, Agent, or Firm*—James P. Hanrath

[57] ABSTRACT

A non-radioactive method of detecting the enzymes beta galactosidase or beta glucosidase directly or for the detection of a ligand and antiligand complex is provided wherein beta galactosidase or the complex labelled with beta galactosidase or a tracer having beta galactosidase conjugated thereto is reacted with 5-bromo-4-chloro-3-indolyl-B-D-galactoside and a tetrazolium salt to produce a colored formazan or a color change indicative of the presence of beta galactosidase, or wherein beta glucosidase or the complex labelled with the beta glucosidase or a tracer having beta glucosidase conjugated thereto is reacted with 5-bromo-4-chloro-3-indolyl-B-D-glucoside and a tetrazolium salt to produce a colored formazan or a color change indicative of the presence of beta glucosidase. Optionally, the galactosidase-galactoside determination or the glucosidase-glucoside determination may further include catalyst phenazine methosulfate (PMS) as a reactant. The preferred tetrazolium salt is dimethylthiazol diphenyl tetrazolium (MTT). A solution or composition of 5-bromo-4-chloro-3-indolyl-B-D-galactoside or 5-bromo-4-chloro-3-indolyl-B-D-glucoside, and a tetrazolium salt, as well as a test kit including the same, is also provided for carrying out the chromogenic method of detection.

16 Claims, 5 Drawing Sheets

ENZYMATIC METHOD FOR DETECTING A LABELLED SEGMENT AND A SOLUTION OR COMPOSITION THEREFOR

CROSS-REFERENCE TO RELATED APPLICATION

This application is a continuation in part of U.S. application Ser. No. 08/010,344 filed Jan. 28, 1993, now U.S. Pat. No. 5,354,658.

BACKGROUND OF THE INVENTION

1. Field of the Invention

The present invention relates to a non-radioactive method and a solution or composition for the detection of the enzymes beta galactosidase or beta glucosidase directly or for the detection of a ligand and antiligand complex of a DNA or RNA nucleic acid, an antigen, a hapten, a protein, an analyte, an antibody, or an antibody complex wherein beta galactosidase or, the complex labelled with beta galactosidase or a tracer having beta galactosidase conjugated thereto, is reacted with 5-bromo-4-chloro-3-indolyl-B-D-galactoside and a tetrazolium salt to produce a colored formazan or a color change indicative of the presence of the labelled complex, or wherein beta glucosidase or the complex labelled with the beta glucosidase or a tracer having beta glucosidase conjugated thereto is reacted with 5-bromo-4-chloro-3-indolyl-B-D-glucoside and a tetrazolium salt to produce a colored formazan or a color change indicative of the presence of the labelled complex. Optionally, the galactosidase-galactoside or glucosidase-glucoside determinations may be reacted with phenazine methosulfate (PMS) as a catalyst in addition to the tetrazolium salt. Preferably the tetrazolium salt is dimethylthiazol diphenyl tetrazolium (MTT).

2. Description of the related art including information disclosed under 37 CFR §§ 1.97–1.99.

Labelling a segment of a DNA or RNA nucleic acid, a protein, a hapten, an antigen, an analyte, an antibody or an antibody complex such that the same can be later identified and detected is desirable in many applications, including diagnostic application of probe technologies.

Assay systems which are both rapid and sensitive have been developed to determine the concentration of a substance, for example an analyte, present in low concentration in a fluid sample. Immunoassays depend on the binding of an antigen or hapten to a specific antibody and have been particularly useful because they give high levels of specificity and sensitivity. Such assays may employ a reagent in labelled form referred to as the tracer.

For example, five basic methods of labelling nucleic acids include nick translation, primer extension, methods based on RNA polymerase, end-labelling methods, and direct labelling methods. In many probe technologies, the need for resolution and sensitivity determines the choice of label to DNA or RNA nucleic acid, proteins, or antibodies. Labels for probes are usually radioactive. Biotin is a commonly used non-radioactive label for probes which can be incorporated into polynucleotide enzymatically using biotinylated nucleotide as the substrate. Alternatively, a photoactivatable analogue of biotin upon brief irradiation with visible light may be used to form stable linkages with both single and double stranded nucleic acids. Biotin-labelled probes are detected through a variety of signal generating systems usually using avidin, a glycoprotein with an extremely high affinity for biotin, or streptavidin, an avidin-like protein. Alternatively, it has been known to label DNA with digoxigenin-labelled deoxyuridine triphosphate. After hybridization to the target DNA, the hybrids are detected by enzyme-linked immunoassay using an antibody conjugate such as biotin-conjugated with alkaline phosphatase.

Non-radioactive labels with biotin have lower sensitivity in comparison with radioactive labels. Thus, radioactive probes are used for most commercial applications of hybridization technologies requiring that probes be freshly prepared at regular intervals due to radioisotopes having short half-lives. Radioactive labels also require special safety precautions for the isotopes and proper radioactive waste disposal.

Enzymes have also often been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

A convenient format for EIA is solid phase immunoassay in which one of the assay reagents is immobilized on a solid support usually in the form of a dip stick, the inside wall of a test tube or cuvette, the well of a microtiter plate, or a microporous membrane. The final step in most membrane EIA procedures employing alkaline phosphatase as an enzyme is contacting a color developing reagent, such as a chromogen, with the membrane. The chromogen reacts with the alkaline phosphatase enzyme captured on the membrane to produce a colored product which may be detected as evidence of the presence of analyte or measured as evidence of the concentration of analyte.

Tetrazolium salts have been used for analytical purposes in the detection of reduced nicotinamideadenine dinucleotide (NADH) wherein the transference of hydrogen is catalyzed not only by enzymes, such as diaphorase, but also by 5-methylphenazinium methylsulphate (PMS) or similar substances, to thereby form deep colored formazans as a reduction indicator. Therefore, appropriate processes have been developed in this way to detect a series of substances which are important in analytical chemistry, via the NADH produced as an intermediate. Tetrazolium salts conventionally employed in dehydrogenase procedures include 3-(4,5-dimethylthiazol-2-yl)-2,4-diphenyl-2H-tetrazolium bromide. (MTT), 2-(p-iodophenyl)-3-(p-nitrophenyl)-5-phenyltetrazolium chloride (INT), 2,2',5,5'-tetra-(p-nitrophenyl)-3,3-(3-dimethoxy-4-diphenylene)-ditetrazolium chloride (TNBT), 2,2'-di-(p-nitrophenyl)-5,5'-diphenyl-3,3'-dimethoxy-4,4'-diphenylene)-ditetrazolium chloride (NBT), 2,2'-p-diphenylene-3,3',5,5'-tetraphenylditetrazolium chloride (neotetrazolium chloride) (NT) and 2,3,5-triphenyltetrazolium chloride (TT).

U.S. Pat. Nos. 4,613,569 and 4,867,196 to Giesler et al. are directed to a stabilized composition of tetrazolium salts containing one to ten moles of a complex-forming acid, such as boric acid or organic hydroxypolylcarboxylic acid, which is soluble in polar solvents per mole of tetrazolium salt. The stabilizing agents are employed in previously known test systems in which the tetrazolium salts are used as indicators such as dehydrogenase procedures involving the detection of lactic acid with lactate dehydrogenase, alcohol with alcohol dehydrogenase, glycerol with glycerol dehydrogenase, glucose with glucose dehydrogenase, acetaldehyde with acetaldehyde dehydrogenase, as well as further systems which can be coupled to the above system.

SUMMARY OF THE INVENTION

According to the present invention there is provided a non-radioactive method of detecting the enzymes beta galactosidase or beta glucosidase directly or for the detection of a ligand and antiligand complex, wherein betagalactosidase or the complex labelled with beta galactosidase or a tracer having beta galactosidase conjugated thereto is reacted with 5-bromo-4-chloro-3-indolyl-B-D-galactoside and a tetrazolium salt to produce a colored formazan or a color change indicative of the presence of beta galactosidase, or wherein beta glucosidase or the complex labelled with the beta glucosidase or a tracer having beta glucosidase conjugated thereto is reacted with 5-bromo-4-chloro-3-indolyl-B-D-glucoside and a tetrazolium salt to produce a colored formazan or a color change indicative of the presence of beta glucosidase. Optionally, the galactosidase-galactoside determination or the glucosidase-glucoside determination may include phenazine methosulfate (PMS) as a catalyst reactant in addition to the tetrazolium salt. Preferably the tetrazolium salt is dimethylthiazol diphenyl tetrazolium (MTT). The present invention also provides for a solution or composition, as well as a test kit including the same, used in the method of detection of the enzyme or enzyme labelled ligand and antiligand complex.

Such a method of detection has great sensitivity, and the reaction, which can be completed in a few minutes to less than a minute, produces a purple formazan or a color change visible by the naked eye in less than one minute as compared to the histochemical determination of beta galactosidase with BCI-galactoside or the histochemical determination of B-glucosidase with BCI-glucoside which may take a few to many hours to produce a color change visible by the naked eye. Further, the present invention requires no radioisotope labelling and its sensitivity and specificity makes it useful for hybridization techniques where radioactive labelling and autoradiography are normally required. Also, the method of detection of the present invention can be used for nucleic acid transfers for colony, plaque, in vitro, and in situ hybridizations including standard Southern, Northern, Western, and Southwestern blotting techniques provided such transfers or techniques utilize beta galactosidase for chromogenic detection. Further, the present invention may not require use of amplification techniques. Further, the present invention requires no stabilizing agent for the tetrazolium salt and produces an irreversible reaction.

DESCRIPTION OF THE PREFERRED EMBODIMENTS

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalence.

The present invention provides a non-radioactive method for detection of the enzymes beta galactosidase and beta glucosidase directly or for the detection of a ligand and antiligand complex of DNA or RNA nucleic acid, a hapten, an antigen, a protein, an antibody, an antibody complex, or an analyte, wherein beta galactosidase or the complex labelled with beta galactosidase or a tracer having beta galactosidase conjugated thereto is reacted with 5-bromo-4-chloro-3-indolyl-B-D-galactoside and a tetrazolium salt to produce a colored formazan or a color change indicative of the presence of the enzyme or enzyme labelled complex, or wherein beta glucosidase or the complex labelled with the beta glucosidase or a tracer having beta glucosidase conjugated thereto is reacted with 5-bromo-4-chloro-3-indolyl-B-D-glucoside and a tetrazolium salt to produce a colored formazan or a color change indicative of the presence of the enzyme or enzyme labelled complex. 5-bromo-4-chloro-3-indolyl-B-D-galactoside (X-gal, molecular weight 408.64, mp 230° (dec.), NMR 2(2),526B, FT-IR 1(2),658B, Disp. A) is the histochemical substrate for beta-galactosidase. 5-bromo-4-chloro-3-indolyl-B-D-glucoside (molecular weight 408.64, mp 249°–251° (dec.), [a]$^{22}$–89.0° (c=1, DMF), FT-IR 1(2),658D, Disp. A) is the histochemical substrate for beta-glucosidase.

Tetrazolium salts which may be employed in the chromogenic determinations of the present invention include 3-(4,5-dimethylthiazolyl-2)-2,5-diphenyl-2H-tetrazolium bromide (MTT), 2-(p-iodophenyl)-3-(p-nitrophenyl)-5-phenyl-tetrazolium chloride (INT), 2,2',5,5'-tetra-(p-nitrophenyl)-3,3-(3-dimethoxy-4-diphenylene)-ditetrazolium chloride (TNBT), 2,2'-di-(p-nitrophenyl)-5,5'-diphenyl-3,3'-dimethoxy-4,4'-diphenylene)-ditetrazolium chloride (NBT), 2,2'-p-diphenylene-3,3',5,5'-tetraphenylditetrazolium chloride (neotetrazolium chloride) (NT) and 2,3,5-triphenyltetrazolium chloride (TT). Dimethylthiazol diphenyl tetrazolium (MTT, 3-(4,5-dimethylthiazol-2-yl)-2,5-diphenyl-2H-tetrazolium bromide, $C_{18}H_{16}N_5SBr$, molecular weight 414.33, mp 195° (dec.), λmax 378 nm, NMR 2,(2),501D, FT-IR 1(2),633B). MTT is the preferred tetrazolium salt for the chromogenic determination of the present invention. Optionally, phenazine methosulfate (PMS, N-methylphenazonium methosulfate, $C_{14}H_{14}N_2O_4S$, molecular weight 306.34, mp 158°–160° (dec), λmax 386 nm, Merck Index 11,6024, FT-IR 1(2),885A) may be used as a catalyst to speed the time of reaction of glucosidase-glucoside or galactosidase-galactoside determination to produce a formazan or color change indicative of the enzyme presence almost instantaneously or within a minute. However use of the PMS catalyst may produce background staining after twenty minutes. The absence of the PMS catalyst will slow the time of reaction such that the formazan or color change will appear within a few minutes with less background staining which for some applications will provide a better visual contrast of the indication of the enzyme.

Figure 1:
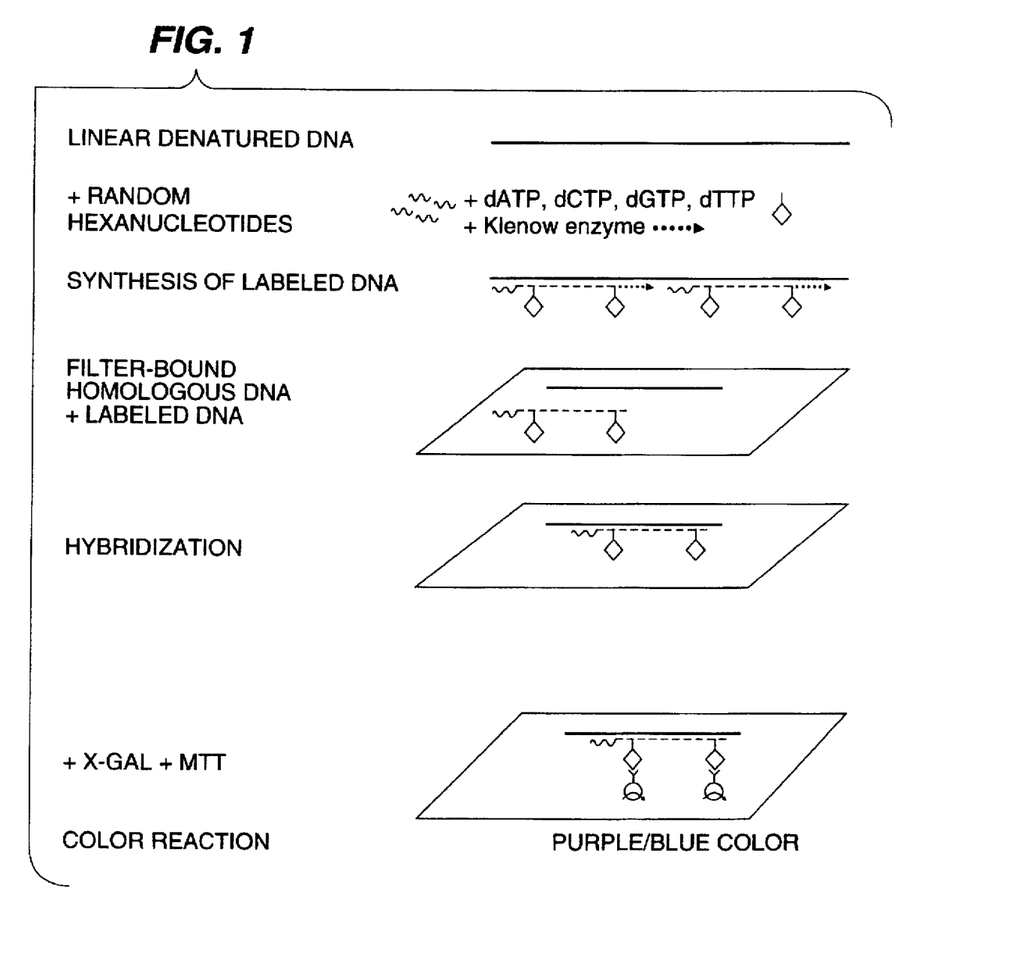
FIG. 1 illustrates the non-radioactive technique of the present invention for the detection of a hybridized DNA segment labelled with beta galactosidase in a color reaction based on 5-bromo-4-chloro-3-indolyl-B-D-galactoside (X-gal) in admixture with dimethylthiazol diphenyl tetrazolium (MTT).
Figure 2:
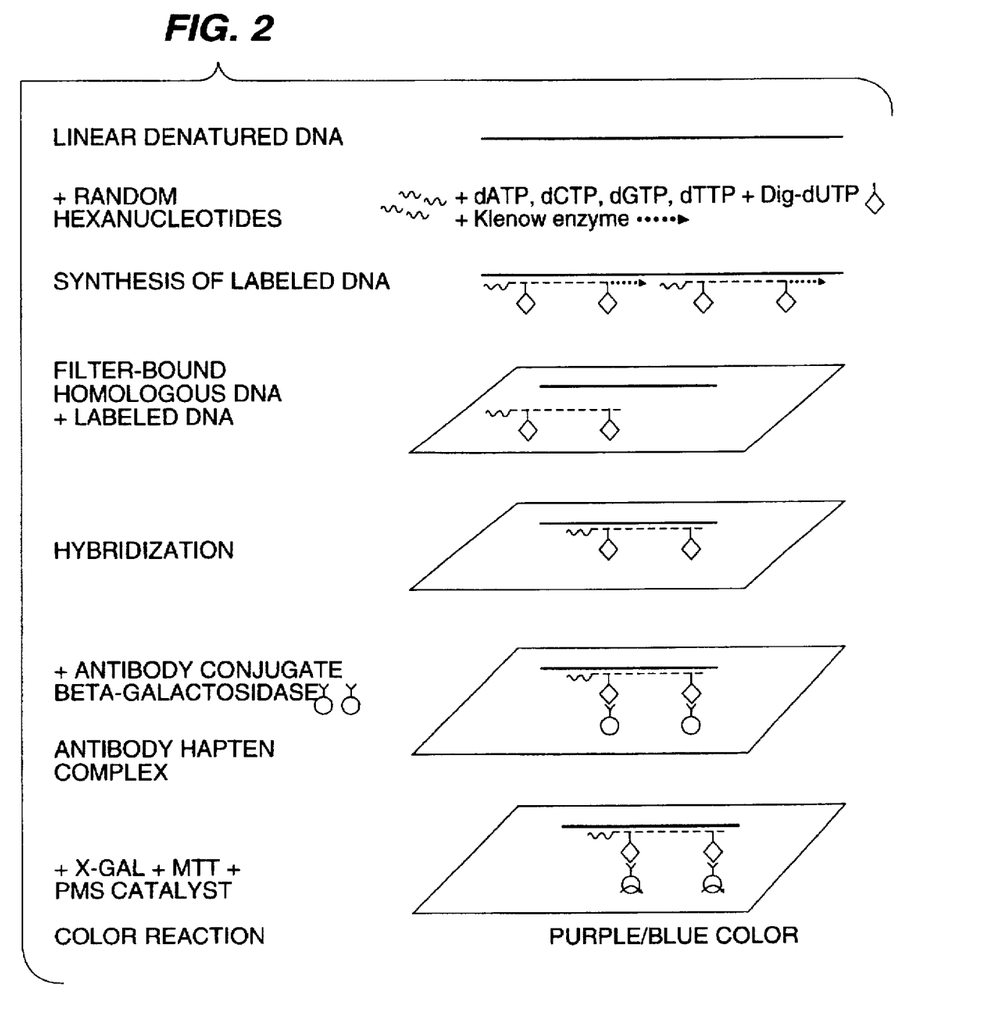
FIG. 2 illustrates the non-radioactive technique of the present invention for the detection of a labelled and hybridized DNA segment using an antibody-conjugate of anti-digoxigenin and beta galactosidase in a color reaction based on 5-bromo-4-chloro-3-indolyl-B-D-galactoside (X-gal) in admixture with dimethylthiazol diphenyl tetrazolium (MTT) and the catalyst phenazine methosulfate (PMS).

The present invention, as illustrated at FIG. 1, detects a hybridized DNA segment labelled with beta galactosidase by a reaction with a mixture of 5-bromo-4-chloro-3-indolyl-B-D-galactoside (X-gal), and dimethylthiazol diphenyl tetrazolium (MTT). In FIG. 2 there is illustrated the detection of a labelled and hybridized DNA segment using an antibody-conjugate of antidigoxigenin and beta galactosidase by a reaction with 5-bromo-4-chloro-3-indolyl-B-D-galactoside (X-gal) and dimethylthiazol diphenyl tetrazolium (MTT) in the presence of a phenazine methosulfate (PMS) catalyst. In both detection methods shown as FIGS. 1 and 2 the dimethylthiazol diphenyl tetrazolium (MTT) serves as a hydrogen acceptor and is converted to $MTTH_2$, a colored purple insoluble formazan complex in stoichiometric quantities which indicates a positive reaction and the presence and concentration of beta galactosidase in the labelled nucleic segment.

Figure 3:
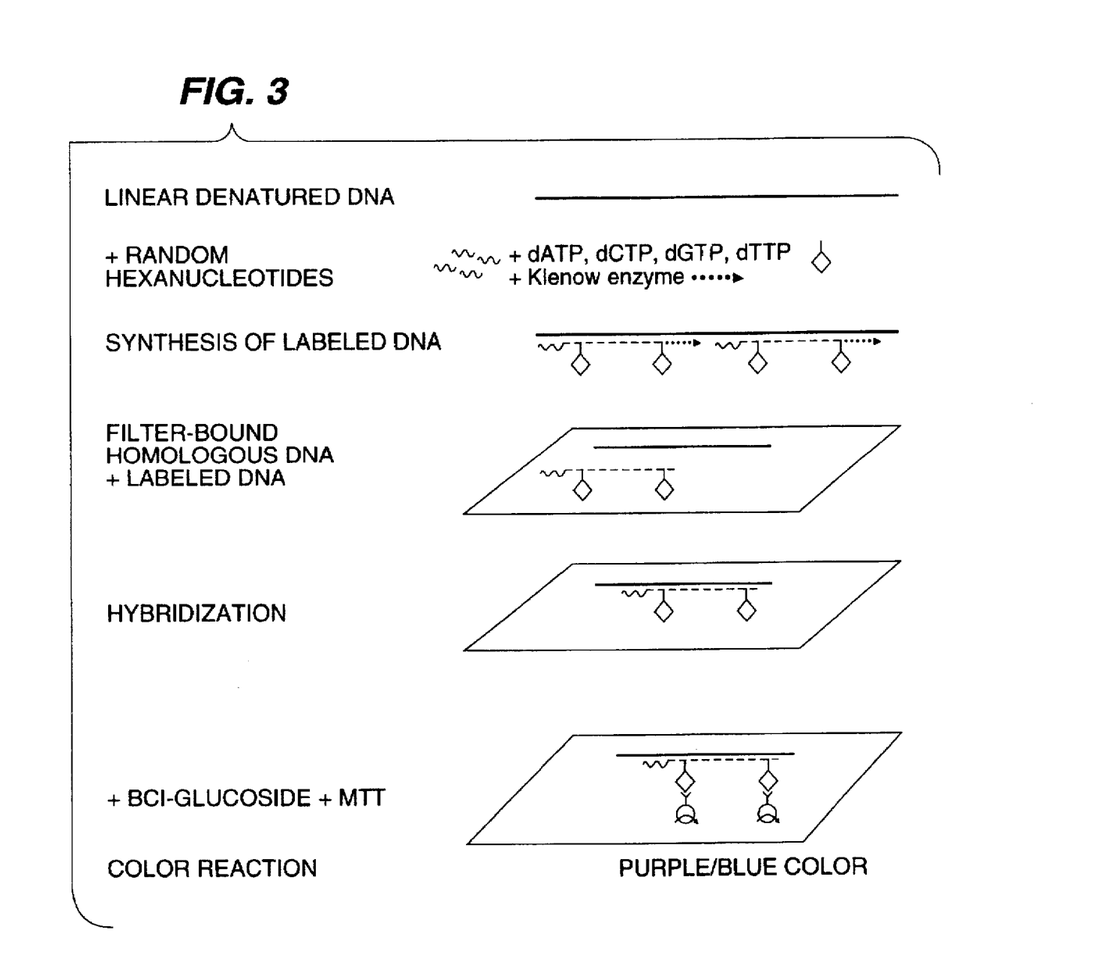
FIG. 3 illustrates the non-radioactive technique of the present invention for the detection of a hybridized DNA segment labelled with beta glucosidase in a color reaction based on 5-bromo-4-chloro-3-indolyl-B-D-glucosidase in admixture with dimethylthiazol diphenyl tetrazolium (MTT).
Figure 4:
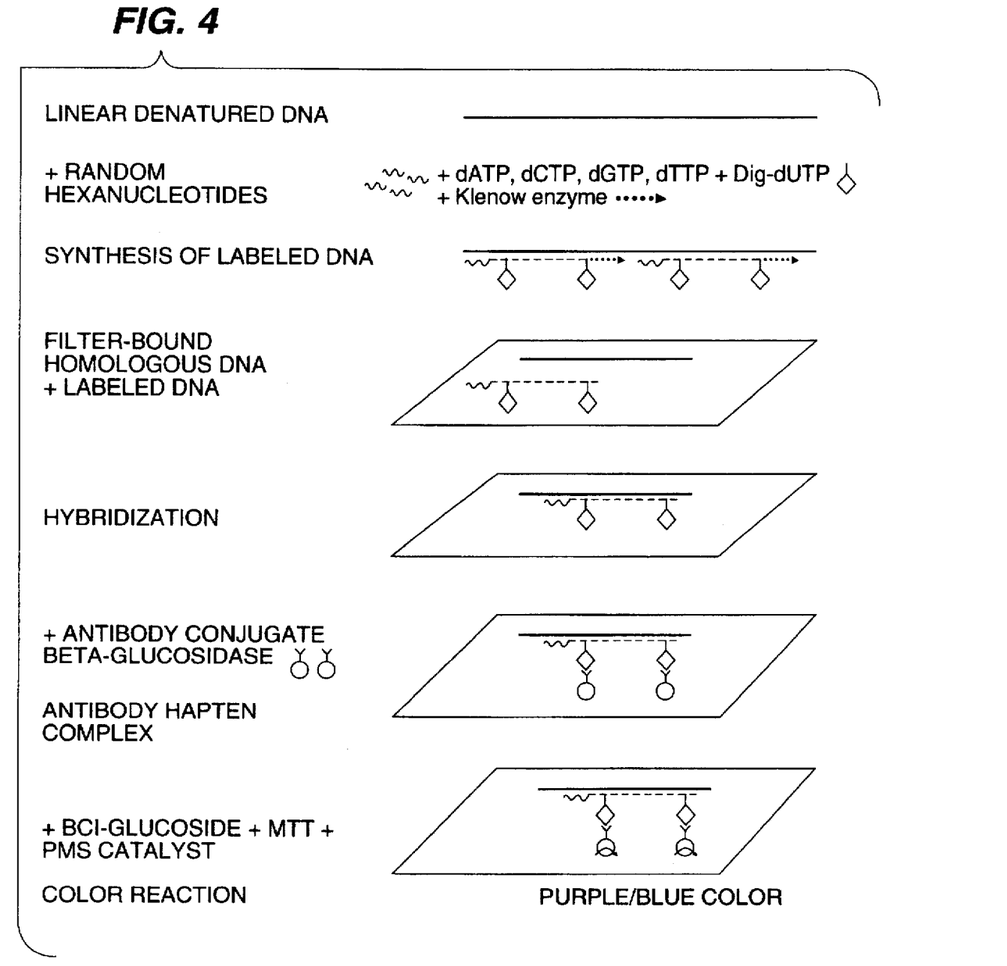
FIG. 4 illustrates the non-radioactive technique of the present invention for the detection of a labelled and hybridized DNA segment using an antibody-conjugate of anti-digoxigenin and beta glucosidase in a color reaction based on 5-bromo-4-chloro-3-indolyl-B-D-glucosidase in admixture with dimethylthiazol diphenyl tetrazolium (MTT) and the catalyst phenazine methosulfate (PMS).
Figure 5:
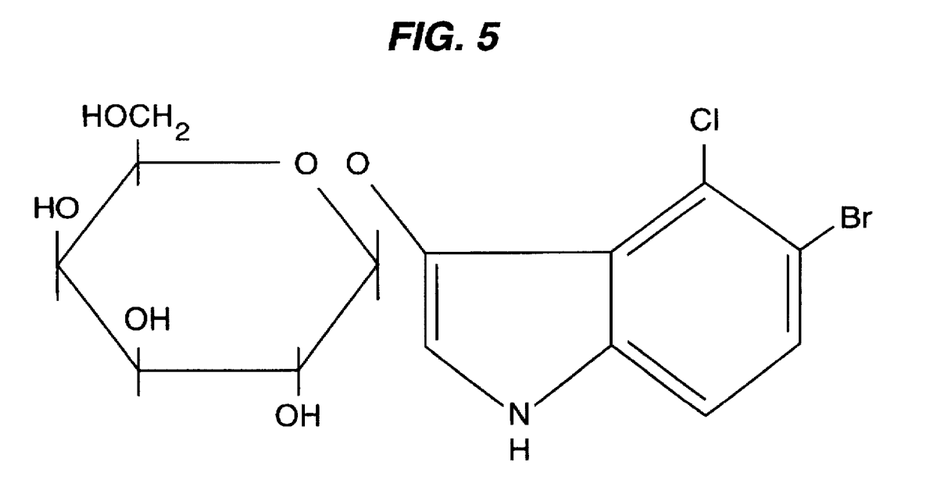
FIG. 5 illustrates the structure of 5-bromo-4-chloro-3-indolyl-B-D-galactoside (X-gal).
Figure 6:
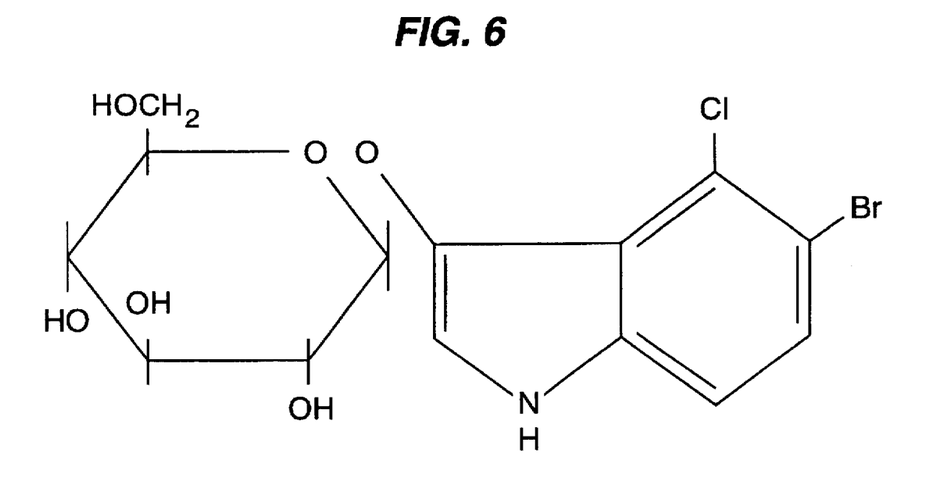
FIG. 6 illustrates the structure of 5-bromo-4-chloro-3-indolyl-B-D-glucosidase.

The chromogenic determination of the present invention illustrated at FIG. 3 detects a hybridized DNA segment labelled with beta glucosidase in a color reaction based on 5-bromo-4-chloro-3-indolyl-B-D-glucosidase in admixture with dimethylthiazol diphenyl tetrazolium (MTT). The nonradioactive technique of the present invention for the detection of a labelled and hybridized DNA segment using an antibody-conjugate of antidigoxigenin and beta glucosidase illustrated at FIG. 4 is a color reaction based on 5-bromo-4-chloro-3-indolyl-B-D-glucosidase in admixture with dimethylthiazol diphenyl tetrazolium (MTT) and the catalyst phenazine methosulfate (PMS). In both detection methods illustrated at FIGS. 3 and 4 the dimethylthiazol diphenyl tetrazolium (MTT) again serves as a hydrogen acceptor and is converted to $MTTH_2$, a colored purple insoluble formazan complex in stoichiometric quantities which indicates a positive reaction and the presence and concentration of beta glucosidase in the labelled nucleic segment.

While immunoassay for a DNA hapten as described above and illustrated at FIGS. 1 through 4 is a preferred application of the invention, one skilled in the art will immediately recognize that the method may be used in many assay procedures. For example, the chromogenic detection of present invention may be implemented in an assay wherein the ligand may be a RNA nucleic acid probe and the tracer may be a complimentary strand of RNA or DNA conjugated with beta galactosidase or beta glucosidase. Alternatively, the ligand may be a protein or antigen using a beta galactosidase or beta glucosidase label or a tracer conjugated with beta galactosidase or beta glucosidase. Still further, the ligand may be an analyte or an antibody or an antibody complex using a beta galactosidase or beta glucosidase label or a tracer conjugated with beta galactosidase or beta glucosidase. Assay procedures involving either direct incorporation of beta galactosidase or beta glucosidase to a ligand or a tracer having beta galactosidase or beta glucosidase conjugated thereto are well known in the art, and so long as beta galactosidase or beta glucosidase is present, the detection method of the present invention involving reacting beta galactosidase or the ligand-antiligand beta galactosidase complex with 5-bromo-4-chloro-3-indolyl-B-D-galactoside or reacting beta glucosidase or the ligand-antiligand beta glucosidase complex with 5-bromo-4-chloro-3-indolyl-B-D-glucoside in admixture with a tetrazolium salt, preferably dimethylthiazol diphenyl tetrazolium (MTT), and optionally catalyzed by phenazine methosulfate (PMS), will provide a reliable chromogenic detection of the presence and concentration of the applicable enzyme or enzyme labelled segment.

Therefore, membranes such as glass fiber, polyvinylidene difluoride, polycarbonate, nitrocellulose and nylon having a ligand bound thereto may be treated with a solution of a tracer with beta galactosidase or beta glucosidase. The tracer may be an antiligand having beta galactosidase or beta glucosidase conjugated to the ligand wherein the assay is performed by conventional sandwich or half sandwich technique. A preferred detection antiligand would be beta galactosidase or beta glucosidase which binds to an antiligand captured on the membrane and thereby affixes the ligand to the membrane surface in direct proportion to the quantity of antiligand in the sample. Alternatively, the ligand may be conjugated by conventional methods to a binder such as biotin, avidin and streptavidin and the latter bound to the antibodies. In any event, the detection method of the present invention provides a chromogenic determination of the presence of the beta galactosidase or beta glucosidase segment respectively by reacting the ligand-antiligand complex with 5-bromo-4-chloro-3-indolyl-B-D-galactoside or 5-bromo-4-chloro-3-indolyl-B-D-glucoside respectively with a tetrazolium salt, preferably dimethylthiazol diphenyl tetrazolium (MTT) optionally catalyzed by phenazine methosulfate (PMS) to form a purple or deep color formazan or produce a color change.

The ligand or antiligand for use with the chromogenic indication of the present invention may be from any source and each may be selected from the group consisting of an antigen, an analyte, a protein, an antibody, an antibody complex, and a hapten. Preferably, if the ligand is an antigen, then the antiligand is an antibody specific for that antigen. Likewise, if the ligand is a hapten, then the antibody preferably is an antibody specific for the hapten. If the ligand is an antibody, preferably the antiligand is an antigen specific for the antibody. If the ligand is a protein, then the antiligand is preferably an antibody specific for the protein. If the ligand is a nucleic acid, then preferably the antiligand is a complementary nucleic acid specific for that nucleic acid. If the ligand is an antibody complex, then the antiligand is preferably an antigen specific for that antibody complex.

For example, the ligand may be an endocrine hormone, such as HCG or FSH, present in body fluid, or it may be isolated from body fluid and subsequently introduced into a different liquid, such as a buffer. If a buffer is used, the pH of the buffer will be between 6 and 8 and preferably is 7.2 for both the galactosidase-galactoside determination and the glucosidase-glucoside determination. In other cases, the ligand may be from a source other than a body fluid, as, for example, a culture of microorganisms such as Chlamydia or a cellar extract thereof. Antibodies, such as the antibody against Lyme disease, may be assayed, or the ligand may be a hapten such as a therapeutic drug or a drug of abuse. The ligand may also be a protein such as glycoprotein 120 useful in HIV testing. Preferred ligands are antigens, most preferably viral antigens present in a body fluid, such as Adenovirus, Parainfluenza 3 virus, Herpes simplex virus (HSV), Respiratory syncytial virus (RSV), and Influenza A (Flu A).

Assay techniques involving the chromogenic indication of the present invention may also be performed by competitive assay wherein the ligand and tracer compete for antiligand binding sites. For example a ligand directly labelled with beta galactosidase or beta glucosidase and a tracer selected from the group consisting of an antigen, an analyte, a protein, an antibody, an antibody complex, and a hapten may compete for binding sites on the antiligand. Alternatively, the competitive assay may be a procedure wherein a ligand selected from the group consisting of an antigen, an analyte, a protein, an antibody, an antibody complex, and a hapten and a tracer having beta galactosidase or beta glucosidase conjugated thereto compete for binding sites on the antiligand. In the latter beta galactosidase or beta glucosidase tracer format, beta galactosidase or beta glucosidase becomes affixed to the membrane surface in inverse proportion to the quantity of ligand in the sample and the absence of colored formazan is indicative of ligand in the sample.

Labelling of ligands with beta galactosidase or beta glucosidase, or labelling of a tracer having beta galactosidase or beta glucosidase conjugated thereto to form a ligand-antiligand complex is well known in the art and deemed to be within the purview of one skilled in the art.

One may, for example, utilize the detection method of the present invention for the identification of a protein synthesized by a recombinant gene by growing cloned bacteria and transferring the same to a membrane, lysing the bacteria with chloroform, binding the first antibody with a protein, and binding a second antibody with a tracer conjugated with beta galactosidase or beta glucosidase such that the presence and concentration of a positive clone-first antibody protein is detected by a color reaction resultant from admixture with the appropriate complimentary 5-bromo-4-chloro-3-indolyl-B-D-galactoside or 5-bromo-4-chloro-3-indolyl-B-D-glucoside and tetrazolium salt, such as dimethylthiazol diphenyl tetrazolium (MTT), with or without phenazine metholsulfate (PMS) as a catalyst.

The present invention of chromogenic detection of a ligand-antiligand complex labelled with beta galactosidase or a tracer having beta galactosidase conjugated thereto may be practiced by reacting the complex with a combined mixture containing 5-bromo-4-chloro-3-indolyl-B-D-galactoside, a tetrazolium salt, such as dimethylthiazol diphenyl tetrazolium (MTT), and optionally phenazine methosulfate (PMS) as a catalyst. The chromogenic detection of the present invention for a ligand-antiligand complex labelled with beta glucosidase or a tracer having beta glucosidase conjugated thereto may be practiced by reacting the complex with a combined mixture containing 5-bromo-4-chloro-3-indolyl-B-D-glucoside, a tetrazolium salt, such as dimethylthiazol diphenyl tetrazolium (MTT), and optionally phenazine methosulfate (PMS) as a catalyst. Such combined mixtures may further include a buffer, such as phosphate buffered saline (PBS), distilled water, or a buffer of a mixture in solution of Tris-HCl or Tris-base, sodium chloride (NaCl), and magnesium chloride (MgCl₂) depending on the specific application of chromogenic determination of the present invention. The buffer will have a pH of about 6 to about 8, with 7.2 being a preferred pH.

In addition to the method set forth above, the present invention includes a solution or composition for practice of the method, as well as a test kit including such solution or composition.

A solution for the detection of the enzyme beta galactosidase directly or for the detection of a ligand and antiligand complex labelled with beta galactosidase or a tracer having beta galactosidase conjugated thereto in a sample to be tested may comprise a mixture of 5-bromo-4-chloro-3-indolyl-B-D-galactoside and a tetrazolium salt, such as dimethylthiazol diphenyl tetrazolium (MTT), and optionally the catalyst phenazine methosulfate (PMS), which when added to said test sample is capable of producing a colored formazan or a color change indicative of the presence of beta galactosidase complex. Such a solution preferably contains equal amounts of phenazine methosulfate (PMS) and dimethylthiazol diphenyl tetrazolium (MTT) or other tetrazolium salt in combination with an excess amount of 5-bromo-4-chloro-3-indolyl-B-D-galactoside. The ratio of 5-bromo-4-chloro-3-indolyl-B-D-galactoside, phenazine methosulfate (PMS), and dimethylthiazol diphenyl tetrazolium (MTT) or other tetrazolium salt respectively in either solution or composition form is preferably about 6:1:1 by weight. A preferred example of the solution would include from about 35 to 50 microliters (hereinafter "ul") of 5-bromo-4-chloro-3-indolyl-B-D-galactoside from a 50 mg/ml aqueous solution, from about 70 to 100 ul of phenazine methosulfate (PMS) from a 10 mM aqueous solution, and from about 70 to 100 ul of dimethylthiazol diphenyl tetrazolium (MTT) from a 10 mM aqueous solution. This preferred solution allows for a more controlled production of colored formazan or color change which is particularly beneficial when working with multiple test samples using beta galactosidase directly or as a label/tracer. However, a solution which would include from about 35 to 50 microliters of 5-bromo-4-chloro-3-indolyl-B-D-galactoside from a 50 mg/ml aqueous solution, from about 100 to 700 ul of phenazine methosulfate (PMS) from a 10 mM aqueous solution, and from about 100 to 700 ul of dimethylthiazol diphenyl tetrazolium (MTT) or other tetrazolium salt from a 10 mM aqueous solution will be sufficient to more quickly produce a colored formazan or color change in reaction with beta galactosidase. The solution may further include a buffer such as phosphate buffered saline (PBS), distilled water or a buffer which is a mixture in solution of Tris-HCl or Tris-base, sodium chloride (NaCl), and magnesium chloride (MgCl₂). The buffered solution will have a pH of about 6 to about 8 with a 7.2 pH being preferred. The solution of the present invention when reacted with beta galactosidase or with a ligand and antiligand complex labelled with beta galactosidase or a tracer having beta galactosidase conjugated thereto in a sample to be tested is capable of producing a colored formazan or a sufficient color change indicative of the presence and/or concentration of the beta galactosidase enzyme or enzyme labelled complex within a minute of contacting the test sample at ambient temperature if the catalyst phenazine methosulfate (PMS) is used and within five minutes if the catalyst is not used. The intensity or degree of color change is sufficient to accurately determine visually or instrumentally the presence and/or concentration of the beta galactosidase enzyme or enzyme labelled complex in the test sample.

A solution for the detection of the enzyme beta glucosidase directly or for the detection of a ligand and antiligand complex labelled with beta glucosidase or a tracer having beta glucosidase conjugated thereto in a sample to be tested would be the same as the solution discussed immediately above with the exception of substituting 5-bromo-4-chloro-3-indolyl-B-D-glucoside for 5-bromo-4-chloro-3-indolyl-B-D-galactoside. Either solution for the galactosidase-galactoside or glucosidase-glucoside determination may employ a tetrazolium salt other than dimethylthiazol diphenyl tetrazolium (MTT).

The present invention also includes a composition for the detection of the enzyme beta galactosidase directly or for the detection of a ligand and antiligand complex labelled with beta galactosidase or a tracer having beta galactosidase conjugated thereto in a sample to be tested comprising a powder or compressed solid or a tablet mixture of 5-bromo-4-chloro-3-indolyl-B-D-galactoside and dimethylthiazol diphenyl tetrazolium (MTT) or other tetrazolium salt, and optionally phenazine methosulfate (PMS) as a catalyst, which, when dissolved in solution and added to said test sample, is capable of producing a colored formazan or a color change indicative of the presence of the beta galactosidase enzyme or enzyme labelled complex. Similarly, a composition for the detection of the enzyme beta glucosidase directly or for the detection of a ligand and antiligand complex labelled with beta glucosidase or a tracer having beta glucosidase conjugated thereto in a sample to be tested comprises a powder or compressed solid or a tablet mixture of 5-bromo-4-chloro-3-indolyl-B-D-glucoside and dimethylthiazol diphenyl tetrazolium (MTT) or other tetrazolium salt, and optionally phenazine methosulfate (PMS) as a catalyst, which, when dissolved in solution and added to said test sample, is capable of producing a colored formazan or a color change indicative of the presence of the beta glucosidase enzyme or enzyme labelled complex. 5-bromo-4-chloro-3-indolyl-B-D-galactoside or 5-bromo-4-chloro-3-indolyl-B-D-glucoside, phenazine methosulfate (PMS), and tetrazolium salts such as dimethylthiazol diphenyl tetrazolium (MTT) naturally exist in a powdered form and may be packaged together in a powder mixture. Alternatively, these powdered ingredients may be compressed into solid form or tableted with an inert carrier, preferably an inert carrier which is soluble in water, such as sucrose or mannitol, by compression or other techniques for tableting known in the tableting arts. The powder or compressed solid or tablet mixture of the composition of the present invention preferably contains approximately equal amounts of phenazine methosulfate (PMS) and dimethylthiazol diphenyl tetrazolium (MTT) or other tetrazolium salt in combination with an excess of 5-bromo-4-chloro-3-indolyl-B-D-galactoside or 5-bromo-4-chloro-3-indolyl-B-D-glucoside. The ratio of 5-bromo-4-chloro-3-indolyl-B-D-galactoside or 5-bromo-4-chloro-3-indolyl-B-D-glucoside, phenazine methosulfate (PMS), and dimethylthiazol diphenyl tetrazolium (MTT) or other tetrazolium salt respectively may also be about 6:1:1 to 1:1:1 by weight.

The present invention may also include a kit of materials for performing the herein disclosed method of detection of beta galactosidase or a ligand and antiligand complex labelled with beta galactosidase or a tracer having beta galactosidase conjugated thereto or the detection of a beta glucosidase or a ligand and antiligand complex labelled with beta glucosidase or a tracer having beta glucosidase conjugated thereto respectively that comprises a solution vial of, or a composition packet of, 5-bromo-4-chloro-3-indolyl-B-D-galactoside or 5-bromo-4-chloro-3-indolyl-B-D-glucoside respectively and a tetrazolium salt such as dimethylthiazol diphenyl tetrazolium (MTT), and optionally the catalyst phenazine methosulfate (PMS), in an amount sufficient, when reacted with said labelled complex, to produce a colored formazan or a color change indicative of the presence of the enzyme or enzyme labelled complex.

The following examples are provided to further describe the invention but are in no way to be considered as limitative of the invention.

EXAMPLE I

A test was made of the reaction of four varying test samples having beta galactosidase. First, 5 ul of beta-galactosidase was introduced to each of 4 polypropylene test tubes (samples A, B, C, D). The beta galactosidase came from Boehringer Mannheim Corporation Lot No. 36-46 having an expiration date of January 1995 and 1,500 activity units. Then, to test tube sample A was introduced 5 ul of 5-bromo-4-chloro-3-indolyl-B-D-galactoside (X-gal), 5 ul of dimethylthiazol diphenyl tetrazolium (MTT) and 5 ul of catalyst phenazine methosulfate (PMS). To test tube sample B was further added 5 ul of distilled water, 5 ul of dimethylthiazol diphenyl tetrazolium (MTT) and 5 ul of catalyst phenazine methosulfate (PMS). Thus, test tube sample B was a control having no 5-bromo-4-chloro-3-indolyl-B-D-galactoside (X-gal). To test tube sample C was further added 5 ul of 5-bromo-4-chloro-3-indolyl-B-D-galactoside (X-gal), 5 ul of distilled water, and 5 ul of catalyst phenazine methosulfate (PMS). To test tube sample D was further added 5 ul of 5-bromo-4-chloro-3-indolyl-B-D galactoside (X-gal), 5 ul of dimethylthiazol diphenyl tetrazolium (MTT), and 5 ul of distilled water. The 5-bromo-4-chloro-3-indolyl-B-D-galactoside (X-gal) used in the experiment came from Boehringer Mannheim Corporation Lot No. GDB 139 having an expiration date of March 1996. The catalyst phenazine methosulfate (PMS) came from a prepared stock solution of 10 mM of phenazine methosulfate. The dimethylthiazol diphenyl tetrazolium (MTT) also came from a prepared stock aqueous solution of 10 mM of dimethylthiazol diphenyl tetrazolium.

Table I generally describes the experiment and the results observed:

TABLE I

| Test Test No. | Contents | Reaction results |
| --- | --- | --- |
| A | X-gal + PMS + MTT | Instantaneous detection color change |
| B | $H_2O$ + PMS + MTT | No detection color change |
| C | X-gal + $H_2O$ + PMS | Faint blue color change after 4 hrs. |
| D | X-gal + MTT + $H_2O$ | Two minute detection color change |

EXAMPLE II

Another experiment was performed using the same protocol of Example I but which instead of test tubes used four test spots of 5 ul of beta galactosidase added to separate locations of one sheet of Whatman filter paper.

Table II below generally describes the experiment and results:

TABLE II

| Test Spot No. | Contents Added | Reaction results |
| --- | --- | --- |
| A | X-gal + PMS + MTT | Instantaneous detection color change |
| B | $H_2O$ + PMS + MTT | No detection color change |
| C | X-gal + $H_2O$ + PMS | Faint blue color change after 4 hrs. |
| D | X-gal + MTT + $H_2O$ | Two minute detection color change |

EXAMPLE III

As a control to Example I above, another experiment was performed using the same protocol of Example I but which instead used lactose (L) instead of 5-bromo-4-chloro-3-indolyl-B-D-galactoside (X-gal). Lactose has a 1–4 beta linkage capable of cleavage with beta galactosidase.

Table III generally describes the experiment and the results:

TABLE III

| Test Tube No. | Contents | Reaction results |
|---|---|---|
| A | L + PMS + MTT | No chromogenic detection |
| B | H₂O + PMS + MTT | No chromogenic detection |
| C | L + H₂O + PMS | No chromogenic detection |
| D | L + MTT + H₂O | No chromogenic detection |

Example III confirms the necessity of using 5-bromo-4-chloro-3-indolyl-B-D-galactoside (X-gal) for the beta galactosidase determination. The lactose for Example III came from vendor Mallinckrodt, Lot No. 119 1498 used in a 25 mg/ml concentration.

EXAMPLE IV

This is a prophetic example relating to the identification of proteins synthesized by recombinant gene. First, a cloned bacteria, such as E-coli is grown and transferred to nitro-cellulose paper or, alternatively, an extraction of proteins from a cloned bacteria is performed by SDS-gel. Next, the E-coli is lysed with chloroform or, alternatively, a western blotting of proteins on the nitrocellulose paper is performed which results in protein being affixed to the nitrocellulose paper from lysed bacteria or SDS-gel respectively. For example, the protein can be a protein of metabolized drug of abuse or a protein of a viral disease. Next, a first antibody, for example an antibody specific for glycoprotein 120 or the antibody against Lyme disease, is bound to the protein to be detected from the cloned bacteria to form a first antibody-protein complex. Next, a second antibody, such as a blotting grade conjugate of goat anti-mouse IgG, goat anti-rabbit IgG, or goat anti-human IgG, conjugated with beta glucosidase is bound to the first antibody-protein complex to form a first and second antibody and beta glucosidase complex. Next, a positive detection of the protein is made by the addition of a solution of 5-bromo-4-chloro-3-indolyl-B-D-glucoside, dimethylthiazol diphenyl tetrazolium (MTT), and the catalyst phenazine methosulfate (PMS) to the complex sufficient to generate a chromogenic deep color change or a purple/blue formazan indicative of the presence and concentration of the protein.

EXAMPLE V

This is a prophetic example relative to a beta-galactosidase/beta-galactoside determination. A test is made of the reaction of four varying test samples having beta glucosidase. First, 5 ul of beta-glucosidase is introduced to each of 4 polypropylene test tubes (samples A, B, C, D). Next, to test tube sample A is introduced 5 ul of 5-bromo-4-chloro-3-indolyl-B-D-glucoside (G1), 5 ul of dimethylthiazol diphenyl tetrazolium (MTT) and 5 ul of catalyst phenazine methosulfate (PMS). To test tube sample B is further added 5 ul of distilled water, 5 ul of dimethylthiazol diphenyl tetrazolium (MTT) and 5 ul of catalyst phenazine methosulfate (PMS). Thus, test tube sample B is a control having no 5-bromo-4-chloro-3-indolyl-B-D-glucoside (G1). To test tube sample C is further added 5 ul of 5-bromo-4-chloro-3-indolyl-B-D-glucoside (G1), 5 ul of distilled water, and 5 ul of catalyst phenazine methosulfate (PMS). To test tube sample D is further added 5 ul of 5-bromo-4-chloro-3-indolyl-B-D glucoside (G1), 5 ul of dimethylthiazol diphenyl tetrazolium (MTT), and 5 ul of distilled water.

Table V generally describes the prophetic results observed:

TABLE VI

| Test Tube No. | Contents | Reaction prophetic results |
|---|---|---|
| A | G1 + PMS + MTT | Instantaneous detection color change |
| B | H₂O + PMS + MTT | No detection color change |
| C | G1 + H₂O + PMS | Faint blue color change after 4 hrs. |
| D | G1 + MTT + H₂O | Two minute detection color change |

The experiments set forth in EXAMPLES I through V above demonstrate the applicability of 5-bromo-4-chloro-3-indolyl-B-D-galactoside (X-gal) and a tetrazolium salt such as dimethylthiazol diphenyl tetrazolium (MTT), and, optionally the catalyst phenazine methosulfate (PMS), to detect a beta galactosidase or a beta galactosidase complex used in any system for detection purpose and 5-bromo-4-chloro-3-indolyl-B-D-glucoside and a tetrazolium salt such as dimethylthiazol diphenyl tetrazolium (MTT), and, optionally the catalyst phenazine methosulfate (PMS), to detect a beta glucosidase or a beta glucosidase complex used in any system for detection purpose. One skilled in the art will therefore appreciate that the method of chromogenic detection of the present invention (and solution and composition therefor) may be used in any system utilizing either beta galactosidase or beta glucosidase or a labelled complex or tracer thereof including, for example, such a system addressed to inorganic analyte detection. It will be understood that the specification and examples are illustrative but not limitative of the present invention and that other embodiments within the spirit and scope of the invention will suggest themselves to those skilled in the art. Many modifications and variations of the invention as heretofore set forth can be made without departing from the scope thereof and therefore only such limitations should be imposed as are indicated by the appended claims.

I claim:

1. A non-radioactive method of detecting beta galactosidase, or a complex having a ligand and an antiligand, said complex being labelled with beta galactosidase, or a tracer having beta galactosidase conjugated thereto in a sample to be tested comprising reacting said sample 5-bromo-4-chloro-3-indolyl-B-D-galactoside and dimethylthiazol diphenyl tetrazolium (MTT) and allowing the reaction to proceed to produce a colored formazan or a color change indicative of the presence of beta galactosidase in said test sample.

2. The method of claim 1 wherein said ligand is selected from the group consisting of an antigen, an analyte, a protein, an antibody, an antibody complex, and a hapten.

3. The method of claim 1 wherein said antiligand is selected from the group consisting of an antigen, an analyte, a protein, an antibody, an antibody complex, and a hapten.

4. The method of claim 2 wherein said ligand is an antigen and said antiligand is an antibody specific for said antigen.

5. The method of claim 2 wherein said ligand is a hapten and said antiligand is an antibody specific for said hapten.

6. The method of claim 2 wherein said ligand is an antibody and said antiligand is an antigen specific for said antibody.

7. The method of claim 2 wherein said ligand is a protein and said antiligand is an antibody specific for said protein.

8. The method of claim 2 wherein said ligand is a nucleic acid and said antiligand is a complimentary nucleic acid specific for said nucleic acid.

9. The method of claim 2 wherein said ligand is an antibody complex and said antiligand is an antigen specific for said antibody complex.

10. The method of claim 1 wherein the amount, intensity, or degree of produced colored formazan or color change is determined visually or instrumentally.

11. The method of claim 1 wherein said test sample is further reacted with the catalyst phenazine methosulfate (PMS).

12. The method of claim 1 wherein said reaction further includes a buffer.

13. The method of claim 12 wherein the buffer has a pH of 6 to 8.

14. The method of claim 13 wherein the buffer has a pH of 7.2.

15. A kit of materials for performing a method of detection of beta galactosidase, or a ligand and antiligand complex labelled with beta galactosidase or a tracer having beta galactosidase conjugated thereto in a sample to be tested according to claim 1, comprising a vial or packet of 5-bromo-4-chloro-3-indolyl-B-D-galactoside and dimethylthiazol diphenyl tetrazolium (MTT) in an amount sufficient, when reacted with said test sample, to produce a colored formazan or a color change indicative of the presence of beta galactosidase in said test sample.

16. The kit of materials of claim 15 wherein the vial or packet further includes phenazine methosulfate (PMS) as a catalyst.

* * * * *

UNITED STATES PATENT AND TRADEMARK OFFICE
CERTIFICATE OF CORRECTION

PATENT NO : 5,670,327
DATED : September 23, 1997
INVENTOR(S): Dennis Wright

It is certified that error appears in the above-identified patent and that said Letters Patent is hereby corrected as shown below:

at Claim 1, column 12 line 42 immediately after the word "sample" insert the word --with--.

Signed and Sealed this

Second Day of December, 1997

Attest:

BRUCE LEHMAN

Attesting Officer

Commissioner of Patents and Trademarks